US006405581B1

(12) United States Patent
Bruhn

(10) Patent No.: US 6,405,581 B1
(45) Date of Patent: Jun. 18, 2002

(54) APPARATUS FOR MEASURING THE CONTENTS OF FOREIGN MATTERS IN A FLUID

(75) Inventor: Ulrik Bruhn, Augustenborg (DK)

(73) Assignee: Danfoss A/S, Nordborg (DE)

( * ) Notice: Subject to any disclaimer, the term of this patent is extended or adjusted under 35 U.S.C. 154(b) by 0 days.

(21) Appl. No.: 09/550,810

(22) Filed: Apr. 18, 2000

(30) Foreign Application Priority Data

Apr. 30, 1999 (DE) .......................................... 199 19 640

(51) Int. Cl.[7] .............................................. G01N 25/18
(52) U.S. Cl. ..................................... 73/61.51; 73/53.01
(58) Field of Search ............................ 73/28.01, 53.01, 73/61.71, 61.72, 61.41, 61.31, 866.5, 431, 322.5

(56) References Cited

U.S. PATENT DOCUMENTS

| | | | | |
|---|---|---|---|---|
| 4,434,650 A | * | 3/1984 | Perry et al. ................. | 73/61.51 |
| 4,935,726 A | * | 6/1990 | Buro et al. ................. | 73/61.51 |
| 5,208,465 A | * | 5/1993 | Jacobson .................... | 250/573 |
| 5,264,368 A | * | 11/1993 | Clarke et al. .............. | 73/61.48 |
| 5,431,047 A | * | 7/1995 | Coha et al. ................. | 73/322.5 |
| 5,966,477 A | * | 10/1999 | Johnson ........................ | 385/12 |
| 6,111,551 A | * | 8/2000 | Schmidt et al. ............. | 343/872 |
| 6,112,592 A | * | 9/2000 | Kathan ......................... | 73/431 |

FOREIGN PATENT DOCUMENTS

GB        2005421 A   * 10/1977

OTHER PUBLICATIONS

Allcock, H. R. and Lampe, F. W., "Contemporary Polymer Chemistry", Prentice Hall, New Jersey, Second Edition (1990), p. 598.*

* cited by examiner

Primary Examiner—Hezron Williams
Assistant Examiner—Michael Cygan
(74) Attorney, Agent, or Firm—Lee, Mann, Smith, McWilliams Sweeney & Ohlson

(57) ABSTRACT

Apparatus for measuring the contents of foreign matters in a fluid, in particular a buoyant apparatus, which has a housing (1) of thermoplastic synthetic material and a hole (4) in the first wall section (2) and a through-hole (5) in a second wall section (3). A sensor (9), arranged in the housing (1) and determined to measure the content of the foreign matter, protrudes into the hole (4). The outer side (10) of the sensor (9) tightly closes the hole (4) with the outer surface of the first wall section (2) and is permeable to the foreign matters that are be measured. Two parts (24,25) of the housing (1) are joined tightly in an area of edge sections (26,27). In order to simplify the manufacturing of this apparatus the two housing parts (24,25) comprise on their inner side an inner wall opposite to the edge sections (26,27) and bridging these, and defining an intermediate space (28) together with the outer wall of the housing (1), the inner wall being made of two wall parts (29) having edges (30) opposite to the edge portions (26,27) of the housing parts (24,25) and abutting one another. The intermediate space (28) is filled with a hardened material which is materially joined with the outer wall and the inner wall.

8 Claims, 4 Drawing Sheets

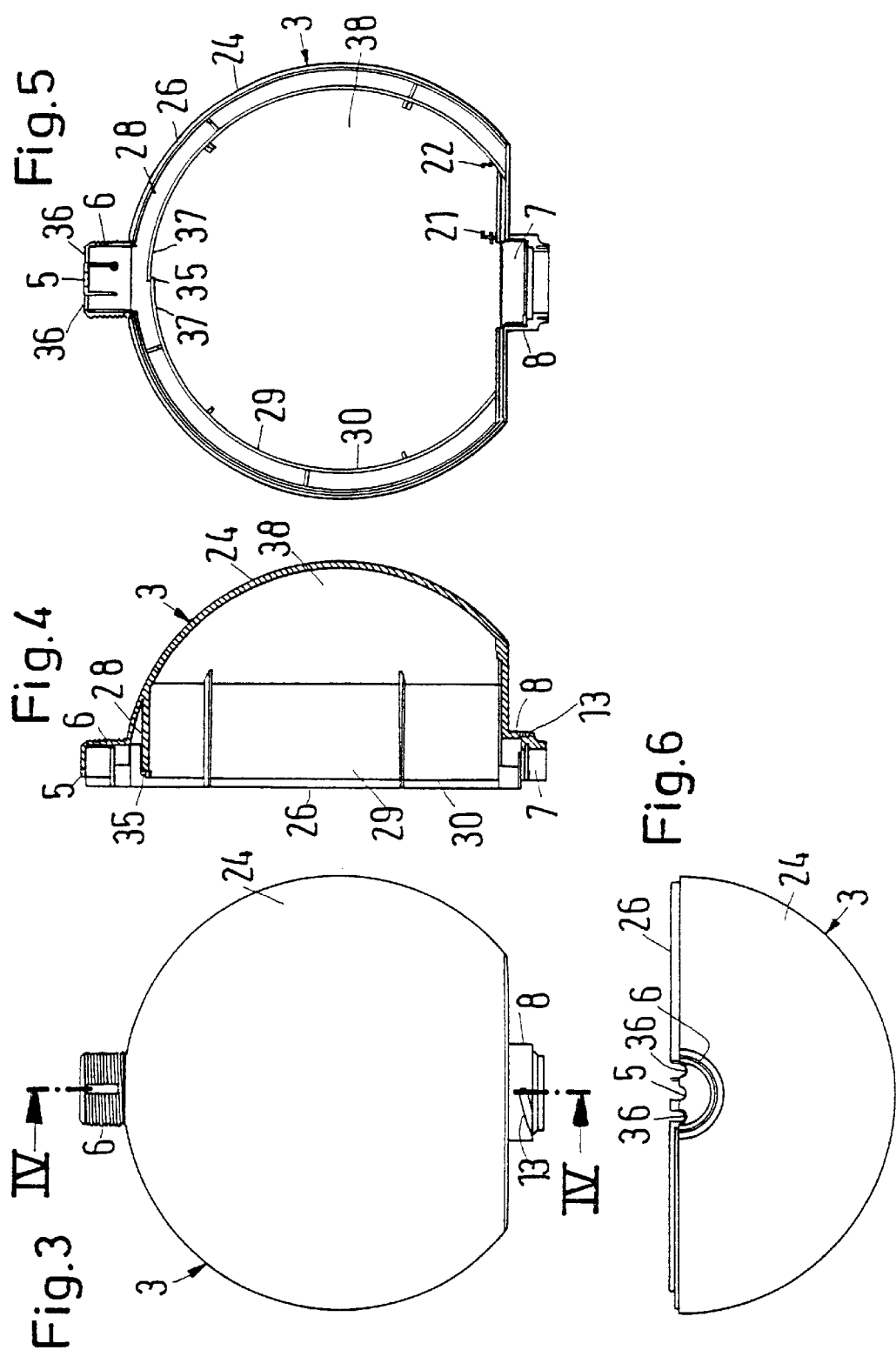

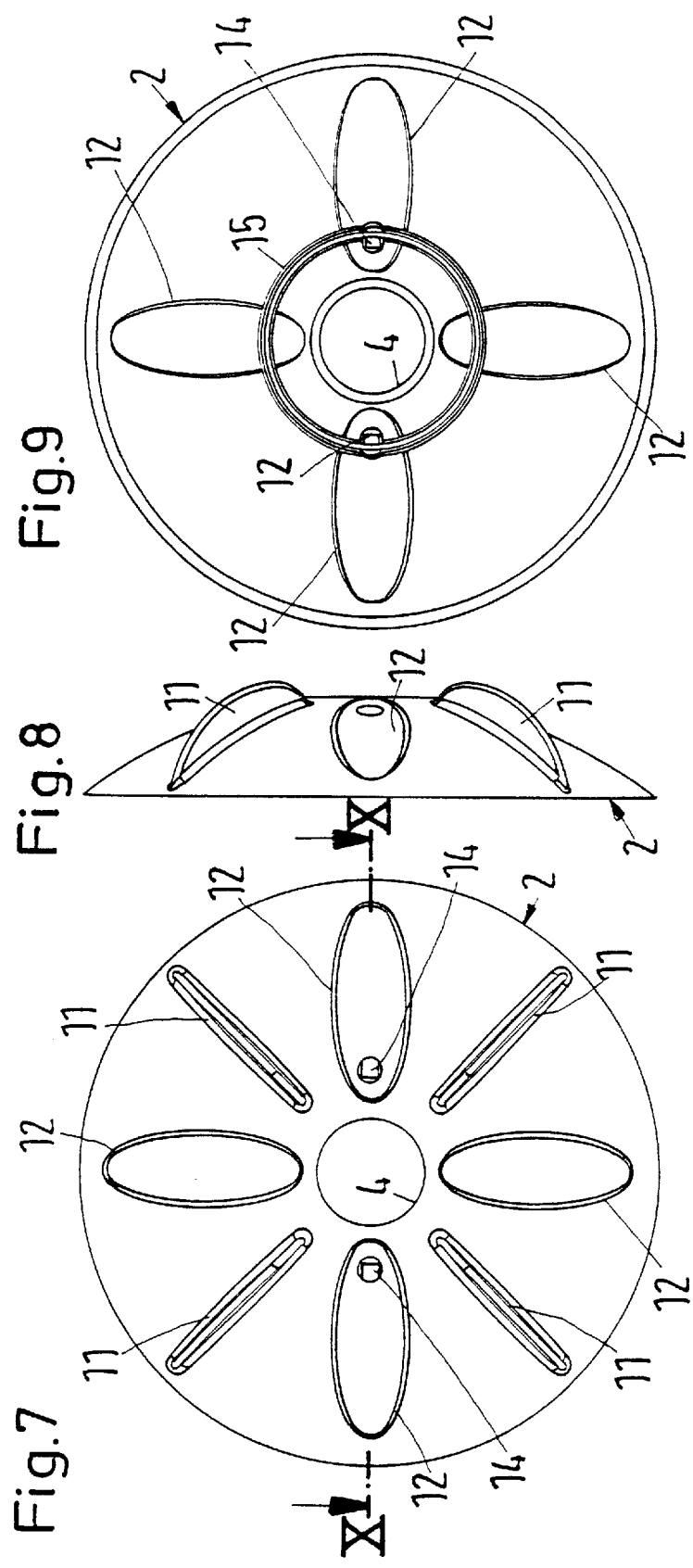

APPARATUS FOR MEASURING THE CONTENTS OF FOREIGN MATTERS IN A FLUID

BACKGROUND OF THE INVENTION

The invention relates to an apparatus for measuring the contents of foreign matters in a fluid, in particular a buoyant apparatus, with a housing of thermoplastic synthetic material and a hole in a first wall section and a through-hole in a second wall section, whereby a sensor for the foreign matter is arranged in the housing and projects in the hole, and whose outer surface tightly closes the hole with the outer side of the first wall section, the sensor, in an area around the hole, being permeable to the foreign matters that are to be measured, and two parts of the housing being joined materially in an area of their edge sections.

An apparatus of this kind is known from GB 2 005 421 A. It serves to analyse wastewater, in particular for the measurement of the oxygen content. Besides, it can be used to measure nutrient solutes in the water, e.g. nitrates and phosphates. The housing is a buoyant hollow ball. The sensor has on its outer side a diaphragm, through which the foreign matter that is to be measured can diffuse. This diaphragm closes the hole, in which the sensor is arranged, tightly with the outer side of the housing. The ball-shaped form of the housing gives the advantage, that it counteracts a contamination of the outer side of the diaphragm, for example fouling or an oil film, when the fluid, that is to be examined, flows. The diaphragm is arched corresponding to the arched shape of the outer surface of the housing, and thereby increases the flow velocity in the area of the diaphragm, in order that contaminations are not easily accumulated there, and therefore will not impair the measuring ability of the sensor. The housing is manufactured in a rotational casting process, whereby the hole in the housing is formed co-axial with the rotating axis. Following this, a through-going inner pipe is adhered to the hole. The sensor has an external screw thread, by means of which it is screwed to an internal thread in one end of a lead-through pipe. Together with the sensor the lead-through pipe is inserted into the adhered inner pipe and fixed to the housing by means of a cap nut.

The manufacturing of this apparatus takes place in several steps and is time-consuming. In particular, the glueing of the housing and the inner pipe increases the manufacturing time due to the required curing time for the adhesive.

Further, in an apparatus of this kind, two halves of the housing has been manufactured in an injection mould process with subsequent bonding by means of ultrasonic welding.

The manufacturing time will hereby be somewhat reduced, however, in both cases two screw connections must not only be manufactured, but also manually handled, both during assembly of the sensor and during replacement of the sensor.

SUMMARY OF THE INVENTION

The object of the invention is to achieve an apparatus of the generic art described in the introduction, which is easier to manufacture.

According to the invention this task has been solved in that both of the housing parts comprise on their inner side an inner wall opposite to the edge sections and bridging these, and defining an intermediate space together with the outer wall of the housing, the inner wall being made of two wall parts having edges opposite to the edge portions of the housing parts and abutting one another, and that the intermediate space is filled with a hardened material which is materially joined with the outer wall and the inner wall.

By using this solution the two housing parts can be manufactured in the same mould, for example in an injection mould process. An electronic circuit for the sensor and its connecting wires can be inserted into the one housing part and the two housing parts can be joined together, or alternatively clipped together. The intermediate space that has been formed in this way can be filled via at least one filling opening with the uncured material which after curing materially joins the outer wall and the inner wall, and at the same time seals the edge sections of the two housing parts in the area of the inner and outer wall.

Preferably, the two housing parts contain polybutylenterephetalate. This material exhibits high strength, stiffness, hardness and lov ductility at low temperatures, while showing dimensional stability at high temperatures. Besides, it has a high resistance and stability towards organic dissolvents, oils and grease.

The heated filling material can be melted together with a corresponding thermoplastic synthetic material of the housing. Preferably though, the material that is filled into the intermediate space is glued together with the synthetic material of the housing.

If the material filled into the intermediate space contains polyurethane, it cannot only be glued easily together with polybutylenterephtalate, but it can also quickly be cured, so that the duration of curing will be short.

In the housing a printed circuit board for the sensor can be arranged and, through at least one sealable opening in the inner wall be encapsulated with the same material as the intermediate space. The filling of the intermediate space and the encapsulation of the printed circuit board can take place in directly successive manufacturing steps, whereby at the same time the hole of the housing which contains the sensor is being sealed from the inside.

The first wall section can form a separate part which is detachably connected with the second wall section. By detaching the first wall section from the second wall section, the sensor can be easily and quickly replaced.

In particular, the sensor can be replaced quickly, if the first wall section has a first lead-through connection piece which surrounds the hole, and which by means of a bayonet socket is connected with a second lead-through connection piece of the second wall section.

The wall sections can both be arched towards the outer side, preferably with a spherical shape. In case of a flowing liquid, a rapid flow around the wall sections is generated, whereby the outer side of the sensor which is formed as a diaphragm is prevented from becoming less permeable or completely impermeable due to a contamination of for example fouling or an oil film, which will lead to malfunction of the apparatus.

BRIEF DESCRIPTION OF THE DRAWINGS

The invention is described hereinafter more detailed with reference to a preferred embodiment in connection with the drawing. Herein shows.

DESCRIPTION OF THE PREFERRED EMBODIMENT

Figure 1:
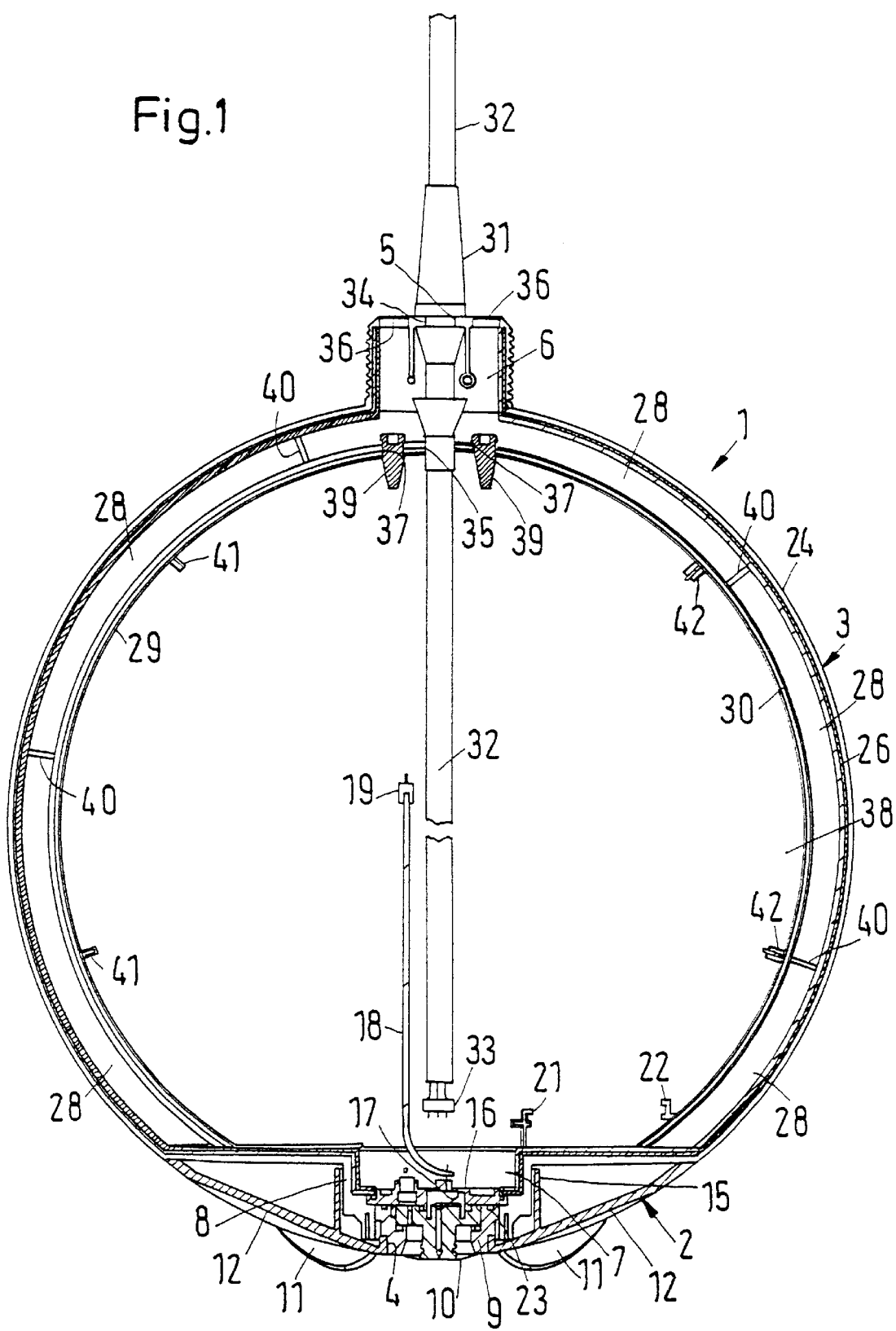
FIG. 1 a cross-section through a measuring apparatus according to the invention, FIG. 2 an explosion drawing of the measuring apparatus according to FIG. 1, FIG. 3 a side view of a somewhat hemispheric housing part of the measuring apparatus according to the invention, FIG. 4 a cut sway view IV—IV of the housing part according to FIG. 3, FIG. 5 an inner view of the housing part according to FIG. 3, FIG. 6 a plan view of the housing part according to FIG. 3, FIG. 7 an outer view of a further housing part of the inventive apparatus, FIG. 8 a side view of the housing part according to FIG. 7, FIG. 9 an inner view of the housing part according to FIG. 7 and FIG. 10 a cut away view X—X of the housing part according to FIG. 7.
Figure 2:
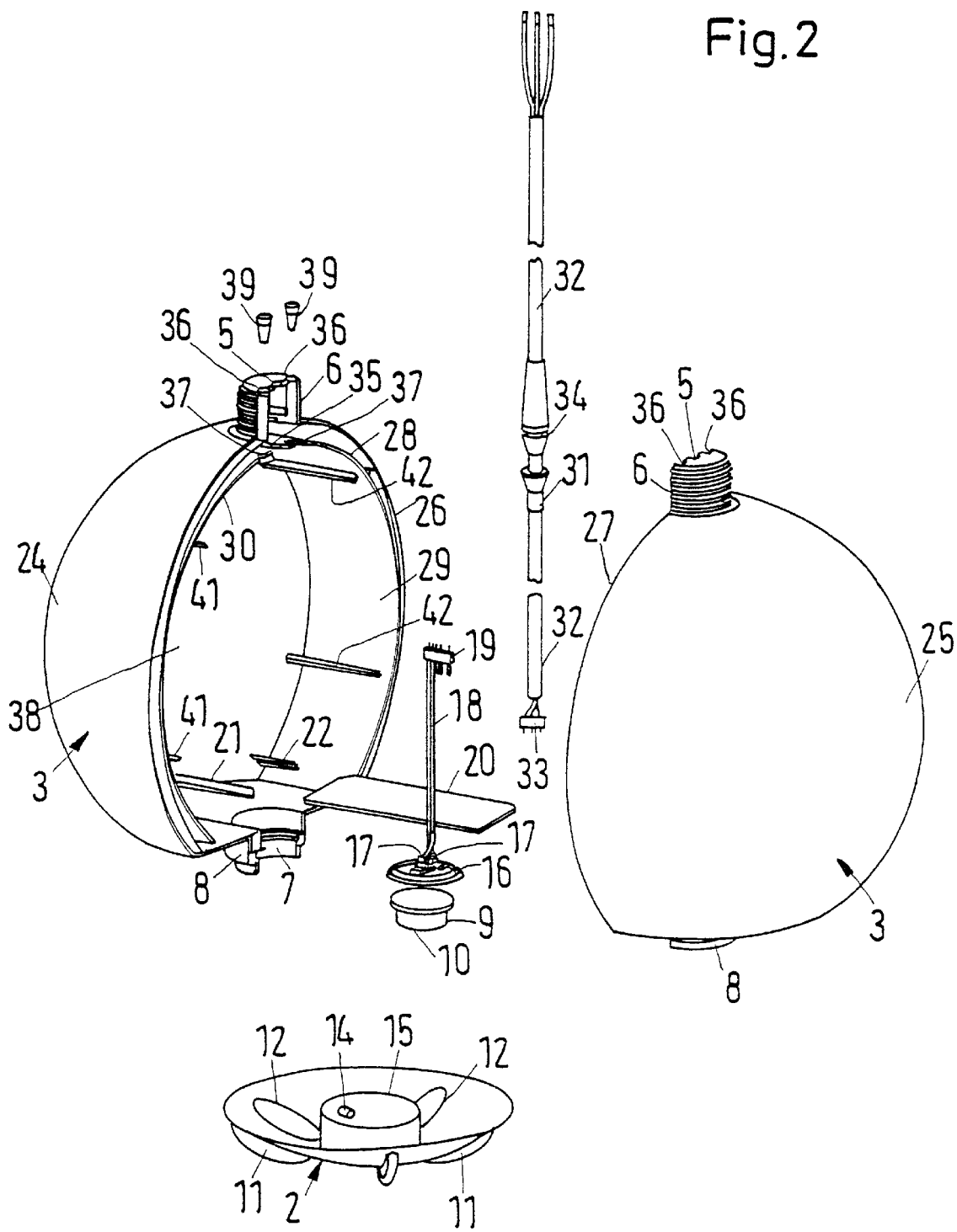

According to FIGS. 1 and 2 an inventive apparatus for measuring the contents of foreign matters as for example oxygen, nitrate or phosphates in a fluid, in particular waste water, comprises a spherical arched housing (1) of thermoplastic synthetic material, preferably polybutylenterephtalate. The housing (1) is to a great extent hollow, which means that the apparatus is buoyant. It has a lower wall section (2), approximately in the form of a section of a hollow ball, and an upper wall section (3). The wall section (2) has a hole (4), and the wall section (3) has an upper through-hole (5) in a connection piece (6), which is provided with external screw thread, and a lower through-hole (7) in a lead-through connection piece (8).

A sensor (9), which is arranged in the housing (1) and described schematically in FIG. 2, protrudes into the hole (4) of the wall section (2). This sensor (9) is the actual measuring cell of the apparatus. The sensor (9) has a diaphragm (10) which is permeable to the foreign matters to be measured, which are dissolved in the fluid. The diaphragm (10) forms the outer side of the sensor (9) and is arched to the outside, whereby it closes tightly with the outer side of the wall section (2).

The arched outer side of the wall section (2) has guiding surfaces (11) for the fluid, protruding radially and extending transversely to the hole (4) (see also FIGS. 7–10). In total there are four guiding surfaces (11), which are arranged at equal angular distances (see FIG. 7), extending radially to the hole and having thin walls, whoose free edges are arched towards the outside. If the apparatus is being placed in a flowing fluid, the guiding surfaces (11) results in that the flow will be concentrated towards the hole (4) and consequently to the diaphragm (10) of the sensor, and the increased velocity of the flow in the area of the diaphragm (10) will to a great extent prevent an accumulation on the outer side of the diaphragm of contaminants that are contained in the water, such as fouling or oil. Thus the permeability of the diaphragm (10) and the measuring ability of the apparatus is maintained for a longer time, as would be the case without the guiding surfaces (11). Four guiding surfaces (11) are shown, however, another number can be chosen.

For optical reasons only, oval grooves (12), which could also be omitted, are placed between the guiding surfaces (11) in the outer side of the wall section (2).

The wall section (2) is detachably connected with wall section (3), which forms the rest of the housing (1), by means of a bayonet socket (13,14), which is formed by the connection piece (8) (see FIGS. 3 and 4) having slots (13) on its outer side of which only one is shown, and radially projecting studs (14) (see FIGS. 7,9 and 10), which are placed on the inner side of a connection piece (15) surrounding the hole (4), which are frictionally engaged in the slots (13). The detachable connection in form of the bayonet socket (13,14) enables a quick replacement of the sensor (9) by unfastening the bayonet socket. For this purpose the built-in sensor (9) is in electrical contact with an essentially plate like connector (16). The connector (16) has contact springs (17), which are connected via a flexible cable (18) and a plug (19) at the free end of the cable to corresponding plug sockets on a printed circuit board (20) shown in a diagram in FIG. 2. To simplify the illustration, the components necessary for the printed circuit board (20) have been left out in the drawing. A sealing ring (23) (FIG. 1) is built in between the sensor (9) and the connector (16).

The wall area (3) consists of two housing parts (24) and (25) which are essentially identical (FIGS. 1–6). The housing parts (24,25) are connectable at their edge sections (26,27) and have on their inner side an inner wall consisting of two essentially identical wall parts (29), of which only one is shown in the FIGS. 1,2,4 and 5, which bridges the edge sections (26,27) in the connected state, and delimits an intermediate space (28) together with the outer wall of the housing (1). The wall parts lie opposite the edge section (26) of the housing parts (24,25) and they meet via their edges when the housing parts (24,25) are connected.

Prior to connecting the housing parts (24,25), a lead-through part (31) for a cable (32), the inner end of which is connected to a plug (33), is inserted into one half of the opening (5) of the connection piece (6), whereby the edge of the opening (5) engages with a circular groove (34) of the lead-through part (31). At the same time the lead-through part (31) is fastened in a passage (35) which is formed in the edges (30) of the inner wall parts (29). Furthermore, the printed circuit board (20) is pushed into the guides of the rails (21,22) and the connector (16) is placed in the opening (7) of the connection piece (8). The plugs (19) and (33) are mounted into corresponding sockets on the printed circuit board (20), and the housing parts (24,25) are connected. Thereafter an age-hardable material in the form of an adhesive polyurethane is filled through the upper part of the connection piece (6) and through the free openings (36) and (37) of the inner wall, which is formed by the wall parts (29). The interior (38) of the housing (1) is at least filled until the printed circuit board (20) and its components are encapsulated. The openings (37) are then sealed by means of rubber-elastic stopper plugs (39) as shown in FIG. 1, whereafter the intermediate space (28) is filled through the openings (36) with the same adhesive material which is not yet age-hardened. The outer wall is connected with the inner wall by means of ribs (40), which serve as stiffening pieces, and have passages (not shown) for the adhesive material, in order that the material can fill out the entire interior (28) between the outer and the inner wall of the housing (1). After the age-hardening of the material in the interior (38) and in the intermediate space (28), the two housing parts (24,25), firstly, and, secondly, the wall parts (29) of the inner wall are sealed and the outer and the inner wall combined with each other, and the printed circuit board (20), including the components mounted, is stably encapsulated.

The housing parts (24,25) and the inner wall parts (29) together with the ribs (40) and the stiffening ribs (41) and (42) on the interior of the wall parts (29) as well as the rails (21,22) can all be produced by injection moulding with one moulding tool, and the same moulding tool can be used for the housing parts (24,25) and the inner wall parts (29).

Further, after having placed the internal parts and connected the housing parts (24,25), the filling of the adhesive material into the interior (38) and the intermediate space (28) as well as the age-hardening of the material can practically take place in the same manufacturing step. Following this, the sensor (9) mounted in the lower wall section (2) can in a simple manner be connected with the connector (16) by connecting the two wall sections (2) and (3) by means of the bayonet socket (13,14).

The production of the measuring apparatus is thus inexpensive and can be carried out quickly. Besides, after opening of the bayonet socket (13,14), the sensor (9) can if necessary be replaced quickly, which however due to the almost automatic cleaning effect by the increased flow velocity between the guide surfaces (11) would be required at much bigger time intervals than without the guide surfaces (11). At the same time the guide surfaces serve as a handle for manipulating the bayonet socket.

At the connecting piece (6) a stationary fastener can be connected which makes it possible to have only the wall section (2) of the measuring apparatus immersed in the flowing fluid. However, the fastener can be omitted, for instance if the fluid is not flowing. In that case the measuring apparatus can be swimming above the water to an extent, that only the lower wall section (2) will immerse into the fluid, firstly because the centre of gravity of the measuring apparatus is just below the centre of the housing (1) and the filler material can be filled extensively into the interior (38). In that case only the lower wall section (2) would be exposed to the fluid and to contamination if the fluid is contaminated.

What is claimed is:

1. Apparatus for measuring the contents of foreign matter in a fluid, the apparatus having a housing consisting of thermoplastic synthetic material, a hole in a first wall section and a through-hole in a second wall section, and a sensor in the hole of the housing for sensing foreign matter, the sensor having outer side which closes the hole tightly with the outer side of the first wall section and, proximate the hole, the sensor being permeable to the foreign matter that is to be measured, the housing comprising two parts joined materially in an area of edge sections, both of the housing parts comprising on their inner side an inner wall which defines an intermediate space together with the outer wall of the housing, the inner wall being made of two wall parts abutting one another, and the intermediate space being filled with a hardened material which is materially joined with the outer wall and the inner wall.

2. Apparatus according to claim 1, in which both housing parts contain polybutyleneterephthalate.

3. Apparatus according to claim 1, in which the material filling the intermediate space is glued to the synthetic material of the housing.

4. Apparatus according to claim 1, in which the material filling the space contains polyurethane.

5. Apparatus according to claim 1, in which a printed circuit board of the sensor is located in the housing and is encapsulated through at least one sealable opening in the inner wall with the same material as that of the intermediate space.

6. Apparatus according to claim 1, in which the first wall section forms a separate part which is detachably connected with the second wall section.

7. Apparatus according to claim 6, in which the first wall section has a first lead-through connection piece which surrounds the hole that is connected with a second lead-through connection piece in the second wall section by means of a bayonet socket.

8. Apparatus according to claim 1, in which the wall sections are arched outwardly.

* * * * *